US011272873B2

(12) United States Patent  
Matsumura et al.

(10) Patent No.: US 11,272,873 B2  
(45) Date of Patent: Mar. 15, 2022

(54) COGNITIVE FUNCTION EVALUATION DEVICE, COGNITIVE FUNCTION EVALUATION SYSTEM, COGNITIVE FUNCTION EVALUATION METHOD, AND RECORDING MEDIUM

(71) Applicant: PANASONIC INTELLECTUAL PROPERTY MANAGEMENT CO., LTD., Osaka (JP)

(72) Inventors: Yoshihiro Matsumura, Osaka (JP); Takashi Okada, Tokyo (JP); Takashi Nishiyama, Hyogo (JP); Kengo Abe, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 328 days.

(21) Appl. No.: 16/339,311

(22) PCT Filed: Sep. 27, 2017

(86) PCT No.: PCT/JP2017/034842  
§ 371 (c)(1),  
(2) Date: Apr. 3, 2019

(87) PCT Pub. No.: WO2018/066421  
PCT Pub. Date: Apr. 12, 2018

(65) Prior Publication Data  
US 2019/0290184 A1 Sep. 26, 2019

(30) Foreign Application Priority Data  
Oct. 7, 2016 (JP) .............................. JP2016-199443

(51) Int. Cl.  
*A61B 5/00* (2006.01)  
*A61B 5/107* (2006.01)  
(Continued)

(52) U.S. Cl.  
CPC .......... *A61B 5/4088* (2013.01); *A61B 5/0077* (2013.01); *A61B 5/1072* (2013.01);  
(Continued)

(58) Field of Classification Search  
CPC ..... A61B 5/107; A61B 5/1071; A61B 5/1072; A61B 5/1077; A61B 5/1079; A61B 5/11;  
(Continued)

(56) References Cited

U.S. PATENT DOCUMENTS 5,724,265 A * 3/1998 Hutchings ............ A43B 3/0005  
235/105  
2012/0101411 A1 4/2012 Hausdorff et al.

FOREIGN PATENT DOCUMENTS

CN 103679171 A 3/2014  
JP 2006-072443 A 3/2006  
(Continued)

OTHER PUBLICATIONS

International Search Report and Written Opinion dated Nov. 7, 2017 in International Application No. PCT/JP2017/034842; with partial English translation.

(Continued)

*Primary Examiner* — Patrick Fernandes  
*Assistant Examiner* — Severo Antonio P Lopez  
(74) *Attorney, Agent, or Firm* — McDermott Will and Emery LLP

(57) ABSTRACT

A cognitive function evaluation device includes an acquisition unit that acquires body motion data representing a body motion of a person to be evaluated during walking; a calculation unit that calculates a displacement of a body of the person to be evaluated during walking based on the acquired body motion data; and an evaluation unit that evaluates a cognitive function of the person to be evaluated based on a frequency peak representing a cycle of walking (Continued)

of person-to-be-evaluated obtained by performing a frequency analysis on the calculated displacement, and to output the evaluation result.

12 Claims, 12 Drawing Sheets

(51) Int. Cl.
  *A61B 5/11* (2006.01)
  *A61B 10/00* (2006.01)
(52) U.S. Cl.
  CPC .............. *A61B 5/11* (2013.01); *A61B 5/112* (2013.01); *A61B 5/1128* (2013.01); *A61B 10/00* (2013.01); *A61B 2576/00* (2013.01)
(58) Field of Classification Search
  CPC .... A61B 5/1113; A61B 5/1114; A61B 5/1116; A61B 5/1118; A61B 5/112; A61B 5/1123; A61B 5/1124; A61B 5/1127; A61B 5/1128; A61B 5/4088; A61B 2562/0219; A61B 2562/0233
  See application file for complete search history.

(56) References Cited

FOREIGN PATENT DOCUMENTS

| JP | 2010-239992 A | | 10/2010 |
|---|---|---|---|
| JP | 2013-059489 A | | 4/2013 |
| JP | 2013059489 A | * | 4/2013 |
| JP | 2013-255786 A | | 12/2013 |
| JP | 2013255786 A | * | 12/2013 |
| JP | 2014-142746 A | | 8/2014 |
| JP | 2015-062654 A | | 4/2015 |
| JP | 2015-066155 A | | 4/2015 |
| JP | 2016-144598 A | | 8/2016 |

OTHER PUBLICATIONS

Search Report and Written Opinion dated Apr. 21, 2020, issued in corresponding Singaporean Patent Application No. 11201902761Y.

* cited by examiner

FIG. 8
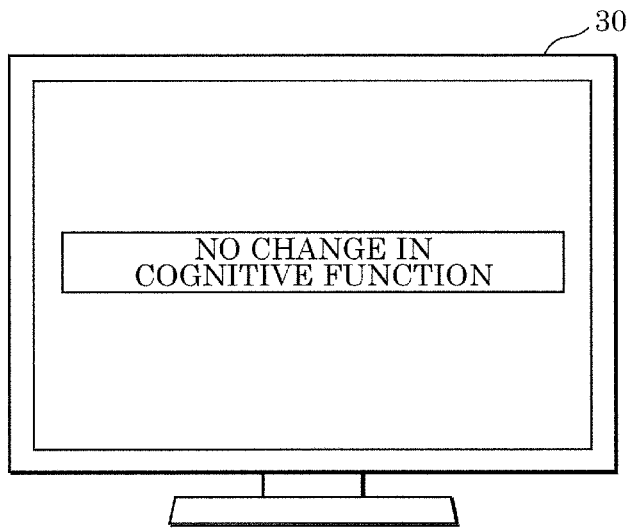
FIG. 9
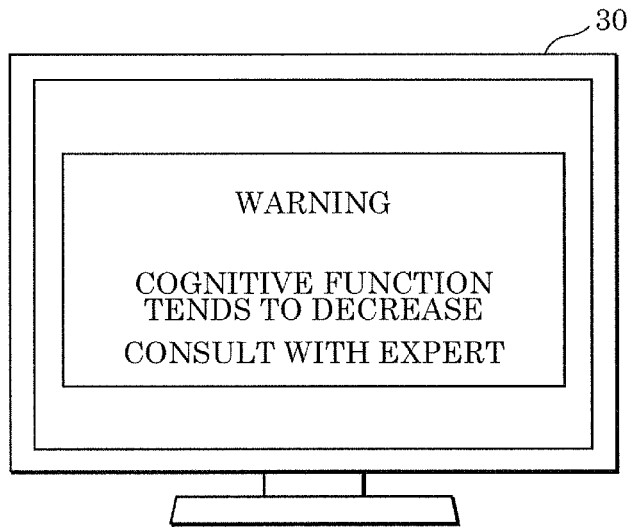
FIG. 10
| PEAK LEVEL OF FREQUENCY PEAK | COGNITIVE FUNCTION |
|---|---|
| L2 OR HIGHER | NORMAL |
| HIGHER OR EQUAL TO L1 AND LOWER THAN L2 | CAUTION (COGNITIVE FUNCTION TENDS TO DECREASE) |
| LOWER THAN L1 | WARNING (COGNITIVE FUNCTION DECREASES) |

COGNITIVE FUNCTION EVALUATION DEVICE, COGNITIVE FUNCTION EVALUATION SYSTEM, COGNITIVE FUNCTION EVALUATION METHOD, AND RECORDING MEDIUM

CROSS-REFERENCE OF RELATED APPLICATIONS

This application is the U.S. National Phase under 35 U.S.C. § 371 of International Patent Application No. PCT/JP2017/034842, filed on Sep. 27, 2017, which in turn claims the benefit of Japanese Application No. 2016-199443 filed on Oct. 7, 2016, the entire disclosures of which Applications are incorporated by reference herein.

TECHNICAL FIELD

The present invention relates to a cognitive function evaluation device, a cognitive function evaluation system, a cognitive function evaluation method, and a recording medium which are capable of evaluating a cognitive function of a person to be evaluated.

BACKGROUND ART

An increase in the number of patients with dementia has become a social problem. Patients showing some signs of dementia notice no symptoms. Accordingly, it is important for their families or a third party to notice the signs of dementia of the patients. As a technique for detecting any change in the life of a resident due to dementia or the like, PTL 1 discloses a life change detection method for detecting a behavior different from the normal behavior of a resident.

CITATION LIST

Patent Literature

PTL 1; Japanese Unexamined Patent Application Publication No. 2006-72443

SUMMARY OF THE INVENTION

Technical Problem

Heretofore, as techniques for evaluating a cognitive function, MMSE (Mini Mental State Examination) and HDS-R (Hasegawa Dementia Scale-Revised) have been known. However, it may be difficult to give a patient (a person to be evaluated) with an unseen health problem the MMSE or HDS-R.

Further, in general, the MMSE or HDS-R is not continuously given to the person to be evaluated, because it places a burden on the person to be evaluated. Accordingly, in the MMSE or HDS-R, it is difficult to continuously monitor a change in the cognitive function and thus it is difficult to detect deterioration in the cognitive function at an early stage.

The present invention provides a cognitive function evaluation device, a cognitive function evaluation system, a cognitive function evaluation method, and a recording medium which are capable of easily evaluating a cognitive function.

Solution to Problem

A cognitive function evaluation device according to an aspect of the present invention includes an acquisition unit configured to acquire body motion data representing a body motion of a person to be evaluated during walking; a calculation unit configured to calculate a displacement of a body of the person to be evaluated during walking based on the body motion data acquired; and an evaluation unit configured to evaluate a cognitive function of the person to be evaluated based on a frequency peak representing a cycle of walking of the person to be evaluated, and to output an evaluation result, the cycle being obtained by performing a frequency analysis on the displacement calculated.

A cognitive function evaluation system according to an aspect of the present invention includes the cognitive function evaluation device, and a body motion data generation device configured to generate the body motion data.

A cognitive function evaluation method according to an aspect of the present invention includes: acquiring body motion data representing a body motion of a person to be evaluated during walking; calculating a displacement of a body of the person to be evaluated during walking based on the body motion data acquired; and evaluating a cognitive function of the person to be evaluated based on a frequency peak representing a cycle of walking of the person to be evaluated, and outputting an evaluation result, the cycle being obtained by performing a frequency analysis on the displacement calculated.

A recording medium according to an aspect of the present invention is a non-transitory computer-readable recording medium having recorded thereon a program for causing a computer to execute the cognitive function evaluation method.

Advantageous Effect of Invention

According to the present invention, it is possible to easily evaluate a cognitive function.

BRIEF DESCRIPTION OF DRAWINGS

FIG. 8 is a diagram illustrating an example of an image indicating that the cognitive function is normal.

FIG. 9 is a diagram illustrating an example of an image indicating that the cognitive function deteriorates.

FIG. 10 is a diagram illustrating an example of reference data.

DESCRIPTION OF EXEMPLARY EMBODIMENTS

Figure 1:
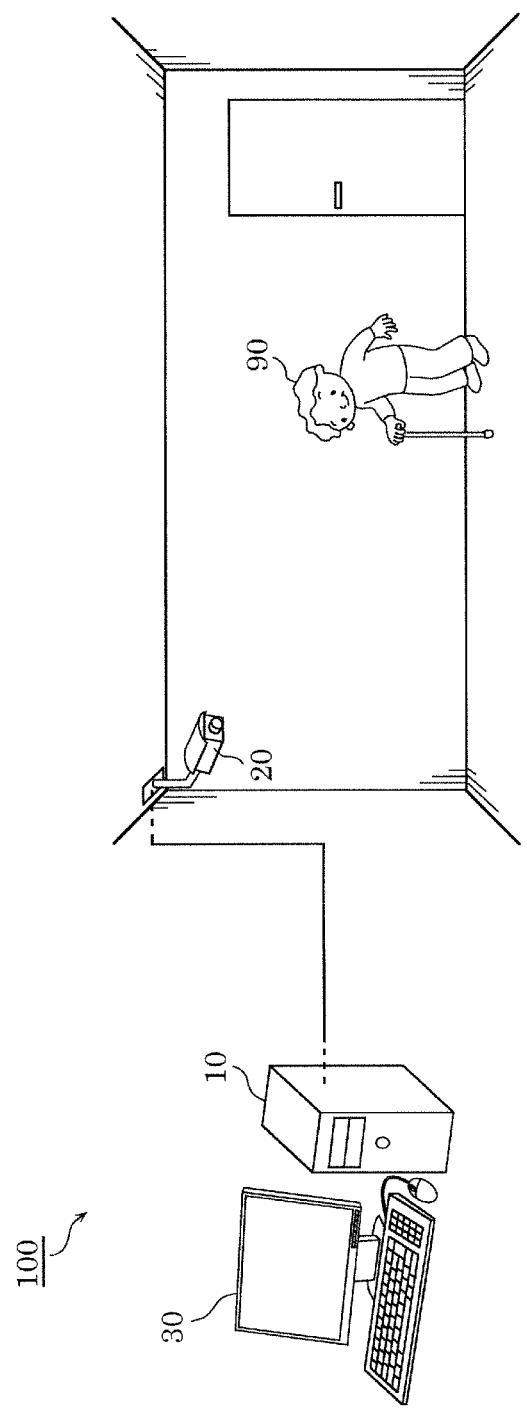
FIG. 1 is a diagram illustrating an outline of a cognitive function evaluation system according to Embodiment 1.

Embodiments will be described below with reference to the drawings. Note that the embodiments described below illustrate comprehensive or specific examples. Values, shapes, materials, components, arrangement positions and connection forms of the components, steps, the order of steps, and the like illustrated in the following embodiments are merely examples, and are not intended to limit the present invention. Furthermore, components that are not described in independent claims each indicating the most generic concept among the components described in the following embodiments are described as arbitrary components.

Note that each figure is a schematic diagram and is not necessarily a precise illustration. Furthermore, in each figure, components that are substantially the same are denoted by the same reference numerals, and repeated descriptions may be omitted or simplified.

Embodiment 1

[Schematic Configuration of Cognitive Function Evaluation System]

The inventors have found that there is a correlation between deterioration in the cognitive function of a person and a walking form of the person. More specifically, the inventors have found that there is a correlation between deterioration in the cognitive function of a person and the periodicity of walking of the person.

A cognitive function evaluation system according to Embodiment 1 is a system that evaluates the cognitive function of a person based on findings by the inventors as described above. FIG. 1 is a diagram illustrating an outline of the cognitive function evaluation system according to Embodiment 1. As illustrated in FIG. 1, cognitive function evaluation system 100 includes cognitive function evaluation device 10, camera 20, and display device 30.

Cognitive function evaluation system 100 generates video data on person-to-be-evaluated 90 during walking that is obtained by camera 20. Camera 20 is installed in, for example, a ceiling or wall of a retirement home or nursing home, and performs continuous image-capturing within a room. Cognitive function evaluation device 10 analyzes the walking form of person-to-be-evaluated 90 based on video data captured (generated) by camera 20, and evaluates the cognitive function of the person to be evaluated. The evaluation result is displayed on display device 30.

Cognitive function evaluation system 100 using camera 20 as described above can evaluate the previous cognitive function and the current cognitive function of person-to-be-evaluated 90 by storing the video data obtained through the continuous image-capturing by camera 20. Furthermore, cognitive function evaluation system 100 can evaluate the cognitive function of person-to-be-evaluated 90 without being noticed by person-to-be-evaluated 90.

[Functional Configuration of Cognitive Function Evaluation System]

Figure 2:
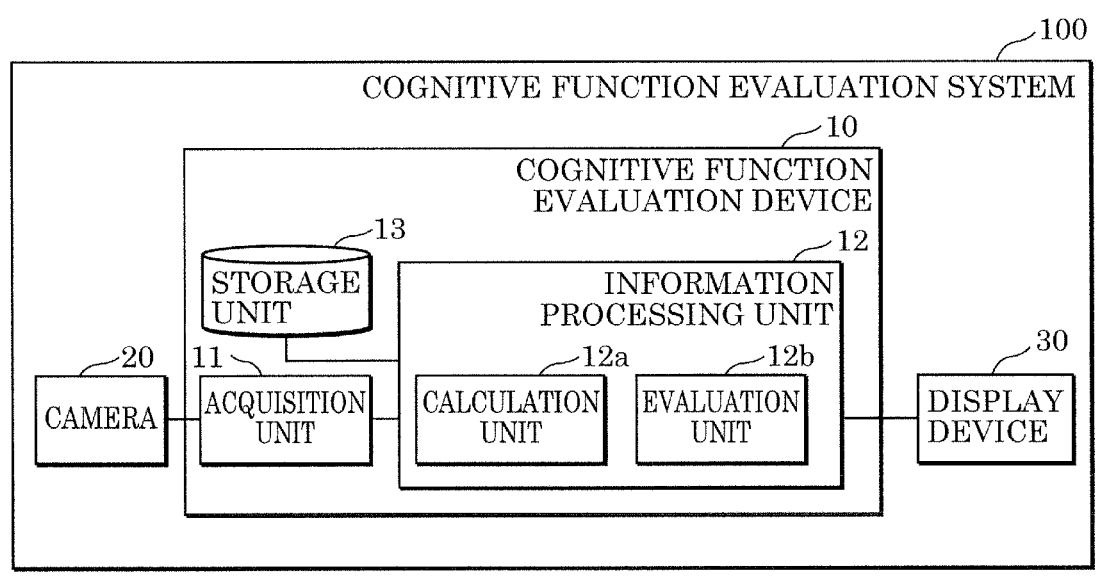
FIG. 2 is a block diagram illustrating a functional configuration of the cognitive function evaluation system according to Embodiment 1.

Next, a functional configuration of cognitive function evaluation system 100 will be described. FIG. 2 is a block diagram illustrating the functional configuration of cognitive function evaluation system 100.

As illustrated in FIG. 2, cognitive function evaluation system 100 includes cognitive function evaluation device 10, camera 20, and display device 30.

Camera 20 is installed in, for example, a ceiling or wall of a retirement home or nursing home, and captures video data on person-to-be-evaluated 90 during walking. Specifically, camera 20 generates video data representing a body motion of person-to-be-evaluated 90 during walking. Camera 20 is an example of a body motion data generation device, and the video data is an example of body motion data. Camera 20 may be a camera using a CMOS (Complementary Metal Oxide Semiconductor) image sensor, or may be a camera using a CCD (Charge Coupled Device) image sensor.

Cognitive function evaluation device 10 analyzes the walking form of person-to-be-evaluated 90 based on the video data captured by camera 20, and evaluates the cognitive function of person-to-be-evaluated 90. Cognitive function evaluation device 10 is, for example, a personal computer, but instead may be a server device. Cognitive function evaluation device 10 may be installed in a building in which camera 20 is installed, or may be installed outside the building. Specifically, cognitive function evaluation device 10 includes acquisition unit 11, information processing unit 12, and storage unit 13.

Acquisition unit 11 acquires the video data captured by camera 20 as body motion data representing a body motion of person-to-be-evaluated 90 during walking. Specifically, acquisition unit 11 is a communication module (communication circuit) that performs wired communication or wireless communication. As long as acquisition unit 11 can communicate with camera 20, the communication method (communication standard, communication protocol) of acquisition unit 11 is not particularly limited. Note that acquisition unit 11 may acquire the video data from storage unit 13. In other words, the video data may be acquired from the inside of cognitive function evaluation device 10, instead of acquiring the video data from the outside of cognitive function evaluation device 10.

Information processing unit 12 performs information processing for evaluating the cognitive function of a user, storage of the video data in storage unit 13, and the like. Specifically, information processing unit 12 includes calculation unit 12a and evaluation unit 12b. Specifically, information processing unit 12 is implemented by a processor, a microprocessor, or a dedicated circuit. Information processing unit 12 may be implemented by a combination of two or more selected from the group consisting of a processor, a microcomputer, and a dedicated circuit.

Calculation unit 12a calculates a displacement of the body of person-to-be-evaluated 90 during walking based on the video data that is acquired by acquisition unit 11 and is stored in storage unit 13. A method for calculating the displacement will be described below.

Evaluation unit 12b evaluates the cognitive function of person-to-be-evaluated 90 based on a frequency peak representing a cycle of walking of person-to-be-evaluated 90 that is obtained by performing a frequency analysis on the calculated displacement, and outputs the evaluation result. The evaluation result is, for example, is image data for displaying the evaluation result as an image on display device 30. However, a specific form of the evaluation result is not particularly limited. A method for evaluating the cognitive function will be described in detail below.

Display device 30 displays an image based on image data (evaluation result) output from evaluation unit 12b. Specifically, display device 30 is a monitor device composed of a liquid crystal panel, an organic EL panel, or the like. As display device 30, an information terminal such as a television set, a smartphone, or a tablet terminal may be used. The communication between evaluation unit 12b and display device 30 is, for example, wired communication. However, when display device 30 is a smartphone or a tablet terminal, the communication between evaluation unit 12b and display device 30 may be wireless communication.

Storage unit 13 is a storage device that stores the video data acquired by acquisition unit 11. Storage unit 13 also stores a program for information processing unit 12 to execute a cognitive function evaluation method, and image data used as the evaluation result of the cognitive function.

Furthermore, storage unit 13 may store reference data representing a relationship between information about a frequency peak representing a cycle of walking of a person and the cognitive function of the person. The reference data is referred to by evaluation unit 12b when the cognitive function of person-to-be-evaluated 90 is evaluated. Specifically, storage unit 13 is implemented by a semiconductor memory, an HDD (Hard Disk Drive), or the like.

[Method for Calculating a Displacement of the Body]

Figure 3:
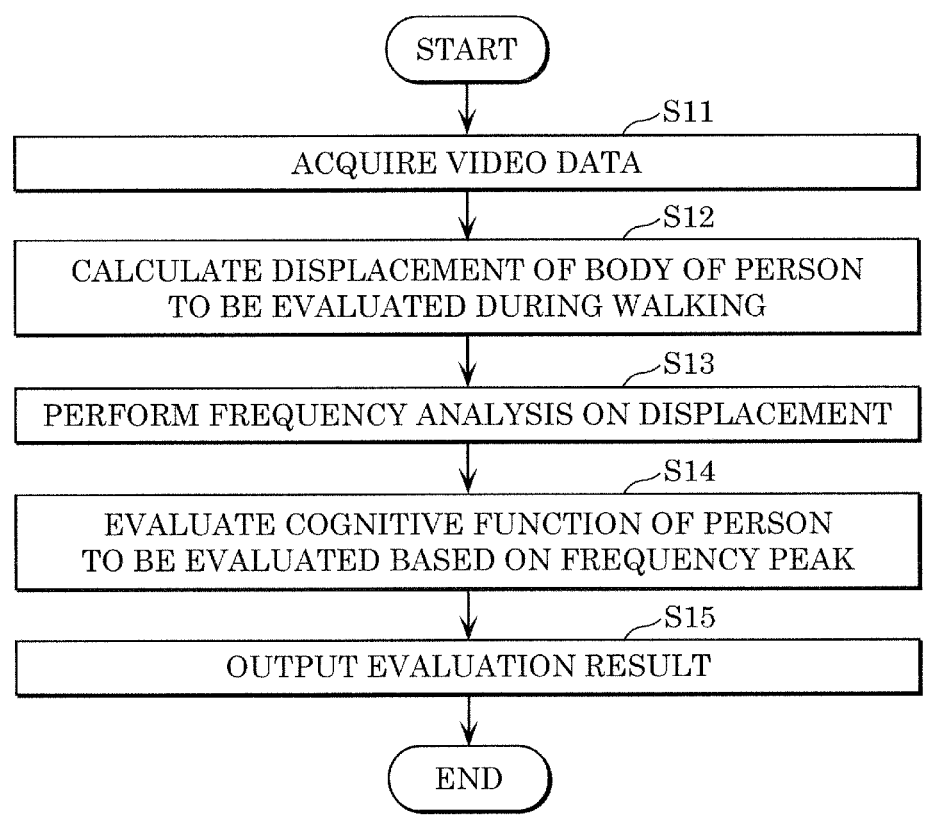
FIG. 3 is a flowchart illustrating a cognitive function evaluation method according to Embodiment 1.

Next, the cognitive function evaluation method to be executed by cognitive function evaluation device 10 (cognitive function evaluation system 100) will be described. FIG. 3 is a flowchart illustrating the cognitive function evaluation method.

First, the method in which calculation unit 12a calculates a displacement of the body of the person to be evaluated will be mainly described in detail. Acquisition unit 11 acquires video data captured by camera 20 as body motion data representing a body motion of person-to-be-evaluated 90 during walking (S11). The video data acquired by acquisition unit 11 is stored in storage unit 13 by information processing unit 12.

Figure 4:
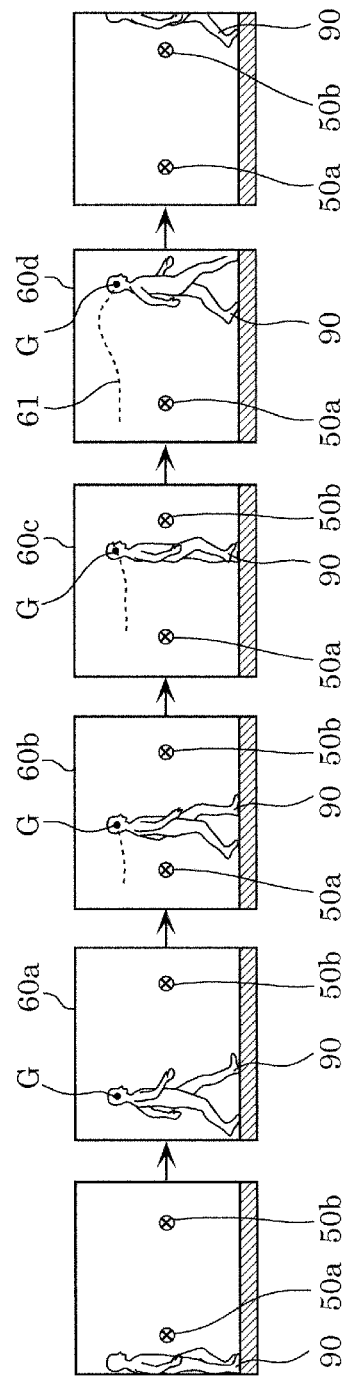
FIG. 4 is a diagram for explaining a method for calculating a displacement in an up-down direction of a body of a person to be evaluated during walking.

Next, calculation unit 12a calculates a displacement of the body of person-to-be-evaluated 90 during walking based on the video data that is acquired and stored in storage unit 13 (S12). More specifically, calculation unit 12a reads out the video data stored in storage unit 13, and performs image processing on the read video data, thereby calculating a displacement in an up-down direction of the body of person-to-be-evaluated 90 during walking. FIG. 4 is a diagram for explaining a method for calculating a displacement in the up-down direction of the body of person-to-be-evaluated 90 during walking.

When camera 20 is installed on a side of person-to-be-evaluated 90, as illustrated in FIG. 4, video data on person-to-be-evaluated 90 during walking is obtained. Note that marker 50a and marker 50b are arranged in an image capturing target space of camera 20. Marker 50a and marker 50b are two markers representing a start point and an end point of a predetermined interval.

Calculation unit 12a first specifies (selects) a processing target frame group from the video data. Specifically, a processing target frame group (frame 60a, frame 60b, frame 60c, and frame 60d) in which frame 60a where marker 50a overlaps person-to-be-evaluated 90 and is hidden is set as a start frame and frame 60d where marker 50b overlaps person-to-be-evaluated 90 and is hidden is set as an end point frame. In other words, in the image processing, calculation unit 12a specifies a period in which person-to-be-evaluated 90 walks on the predetermined interval represented by the two markers in the video data. Note that whether person-to-be-evaluated 90 overlaps marker 50a can be determined by detecting a change in the pixel value corresponding to the position of marker 50a. Whether person-to-be-evaluated 90 overlaps marker 50b can also be determined in the same manner.

Next, calculation unit 12a detects the position of person-to-be-evaluated 90 in each frame (frames 60a to 60d) in the specified processing target frame group. Calculation unit 12a can detect the position of person-to-be-evaluated 90 in each of frames 60a to 60d based on, for example, a difference between each of specified frames 60a to 60d and a reference frame, which is a still image, when there is no person in an image-capturing range of camera 20. The reference frame is preliminarily stored in, for example, storage unit 13. Note that other methods such as edge detection, or pattern matching based on a statistical method, may be used to detect the position of person-to-be-evaluated 90 in each of frames 60a to 60d.

Figure 5:
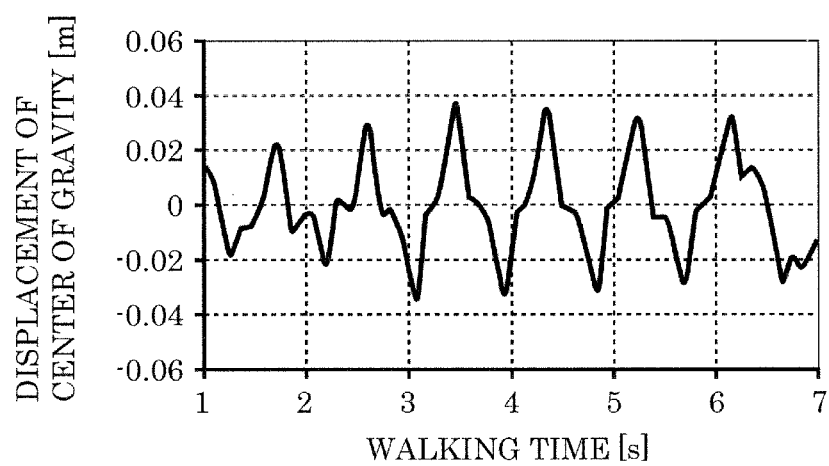
FIG. 5 is a diagram illustrating a displacement in the up-down direction of the body of the person to be evaluated during walking.

Next, calculation unit 12a specifies the position of a head portion of person-to-be-evaluated 90 by applying a circular or elliptical pattern to an upper end portion of the detected position of person-to-be-evaluated 90. Furthermore, calculation unit 12a determines a central position of the applied pattern as center-of-gravity position G. Calculation unit 12a can specify temporal change 61 in the up-down direction of center-of-gravity position G in the processing target frame group. In other words, temporal change 61 is a swing in the up-down direction of the body of person-to-be-evaluated 90 during walking. As a result, calculation unit 12a can calculate a signal as illustrated in FIG. 5 as a displacement in the up-down direction of the body of person-to-be-evaluated 90 during walking. FIG. 5 is a diagram illustrating a displacement in the up-down direction of the body of person-to-be-evaluated 90 during walking.

Note that FIG. 4 described above schematically illustrates the video data when camera 20 is arranged on a side of person-to-be-evaluated 90. However, in practice, it is assumed that camera 20 installed in a ceiling or the like of a building images person-to-be-evaluated 90 with an angle at which person-to-be-evaluated 90 is looked down from above. In this case, calculation unit 12a may perform projection transformation on each frame included in the video data to generate video data as illustrated in FIG. 4. A transformation equation used for projection transformation is preliminarily stored in, for example, storage unit 13.

Furthermore, in the method for calculating the displacement of the body as described above, the displacement of the head portion of person-to-be-evaluated 90 is detected, but instead a displacement of a region other than the head portion of person-to-be-evaluated 90 may be detected. As described below, in the evaluation of the cognitive function, the frequency peak representing the cycle of walking is used. Accordingly, a region (e.g., another region of the upper body of person-to-be-evaluated 90) in which the frequency peak can be appropriately obtained may be detected. Note that when the head portion is detected, the head portion may be detected using a face recognition technique. Alternatively, a center-of-gravity position of a recognition area may be detected as the center-of-gravity position of a human by using a human recognition technique.

Instead of the displacement in the up-down direction of person-to-be-evaluated 90, a displacement in a right-left direction of person-to-be-evaluated 90 or a displacement in a front-back direction of person-to-be-evaluated 90 may be used. In this case, image processing such as projection transformation is also performed as needed depending on the installation position of camera 20.

[Cognitive Function Evaluation Method]

Next, a method for evaluating a cognitive function by evaluation unit 12b will be described below with reference to FIG. 3. Evaluation unit 12b performs a frequency analysis on the displacement calculated by calculation unit 12a (S13). Specifically, evaluation unit 12b performs discrete Fourier transform on the displacement of the body (signal indicating a temporal change in the position of the body as illustrated in FIG. 5) calculated by calculation unit 12a. In other words, evaluation unit 12b performs frequency conversion processing for converting the signal indicating the displacement of the body from a temporal region into a frequency region.

Figure 6:
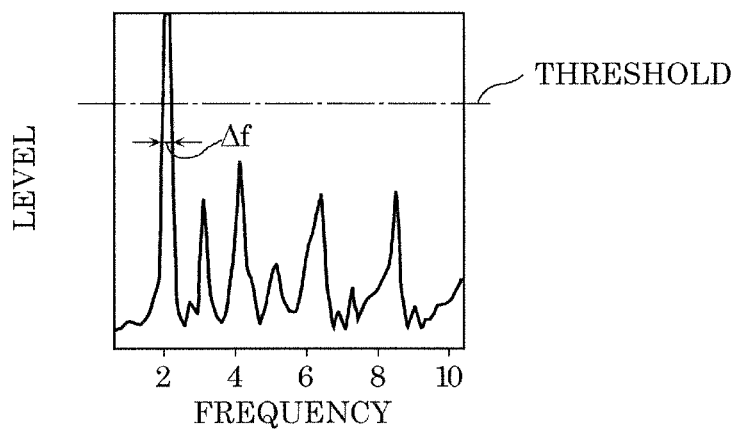
FIG. 6 is a diagram illustrating a frequency analysis result when a cognitive function of the person to be evaluated is normal.
Figure 7:
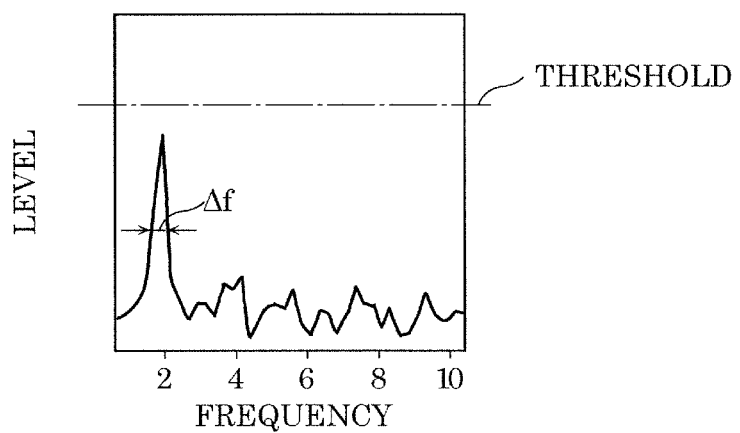
FIG. 7 is a diagram illustrating a frequency analysis result when the cognitive function of the person to be evaluated deteriorates.

When the cognitive function of person-to-be-evaluated 90 is normal, the analysis result as illustrated in FIG. 6 is obtained. When the cognitive function of person-to-be-evaluated 90 deteriorates, the analysis result as illustrated in FIG. 7 is obtained. FIG. 6 is a diagram illustrating the frequency analysis result when the cognitive function of person-to-be-evaluated 90 is normal. FIG. 7 is a diagram illustrating the frequency analysis result when the cognitive function of person-to-be-evaluated 90 deteriorates.

In both of the analysis results illustrated in FIG. 6 and FIG. 7, a peak with a lowest frequency (peak with a highest level) is a frequency peak representing a cycle of walking. In other words, the peak with the lowest frequency is a main frequency component. If the cognitive function of person-to-be-evaluated 90 is normal, person-to-be-evaluated 90 can walk at a constant cycle. Accordingly, in FIG. 6, the frequency peak representing the cycle of walking is sharper than that illustrated in FIG. 7 and the peak level is higher than that in FIG. 7.

On the other hand, when the cognitive function of person-to-be-evaluated 90 deteriorates, it is difficult for person-to-be-evaluated 90 to walk at a constant cycle, and thus a variation in the cycle of walking increases. Therefore, in FIG. 7, the peak level of the frequency peak representing the cycle of walking is lower than that illustrated in FIG. 6, and the skirt of the frequency peak is wider than that in FIG. 6.

Accordingly, evaluation unit 12b evaluates the cognitive function of person-to-be-evaluated 90 based on the frequency peak representing the cycle of walking of person-to-be-evaluated 90 that is obtained by the frequency analysis obtained by discrete Fourier transform (S14).

For example, evaluation unit 12b evaluates the cognitive function of person-to-be-evaluated 90 based on the peak level of the frequency peak. Evaluation unit 12b evaluates that the cognitive function of the person-to-be-evaluated deteriorates as the peak level decreases. For example, when the peak level is higher than or equal to a threshold (illustrated in FIG. 6 and FIG. 7), evaluation unit 12b determines that the cognitive function is normal and outputs image data (evaluation result) for displaying that the cognitive function is normal (S15). As a result, display device 30 displays an image as illustrated in FIG. 8. FIG. 8 is a diagram illustrating an example of the image representing that the cognitive function is normal.

On the other hand, for example, when the peak level is less than the threshold, evaluation unit 12b determines that the cognitive function deteriorates, and outputs image data (evaluation result) for displaying that the cognitive function deteriorates (S15). As a result, display device 30 displays an image as illustrated in FIG. 9. FIG. 9 is a diagram illustrating an example of the image representing that the cognitive function deteriorates.

Note that evaluation unit 12b may evaluate the cognitive function of person-to-be-evaluated 90 based on a half width $\Delta f$ (illustrated in FIG. 6 and FIG. 7) of the frequency peak. Evaluation unit 12b evaluates that the cognitive function of the person to be evaluated deteriorates as the half width $\Delta f$ increases. For example, when the half width $\Delta f$ is less than the threshold, evaluation unit 12b determines that the cognitive function is normal, and outputs image data (evaluation result) for displaying that the cognitive function is normal (S15). As a result, display device 30 displays an image as illustrated in FIG. 8.

On the other hand, for example, when the half width $\Delta f$ is greater than or equal to the threshold, evaluation unit 12b determines that the cognitive function deteriorates, and outputs image data (evaluation result) for displaying that the cognitive function deteriorates (S15). As a result, display device 30 displays an image as illustrated in FIG. 9.

Note that in the above description, the cognitive function is evaluated at two levels, but instead may be evaluated at three or more levels (e.g., three levels of a normal level, a caution level, and a warning level) by setting two or more thresholds with different values. The thresholds may be set by obtaining a correlation by preliminarily performing calculation of a cognitive function scale, such as MMSE or HDS-R, and the peak level (or half width $\Delta f$) of the frequency peak representing the cycle of walking on a plurality of persons-to-be-evaluated 90.

Furthermore, the thresholds may be included in an evaluation algorithm (program) of evaluation unit 12b, or may be stored in storage unit 13 as reference data. FIG. 10 is a diagram illustrating an example of the reference data.

As illustrated in FIG. 10, the reference data represents the relationship between the cognitive function of a person and information about the frequency peak representing the cycle of walking of the person. In the example of FIG. 10, the information about the frequency peak is the peak level of the frequency peak, but instead may be the half width $\Delta f$ of the frequency peak.

Then, evaluation unit 12b may compare the frequency peak representing the cycle of walking of person-to-be-evaluated 90 to the reference data stored in storage unit 13, to thereby evaluate the cognitive function of person-to-be-evaluated 90.

Modified Example of Embodiment 1

Figure 11:
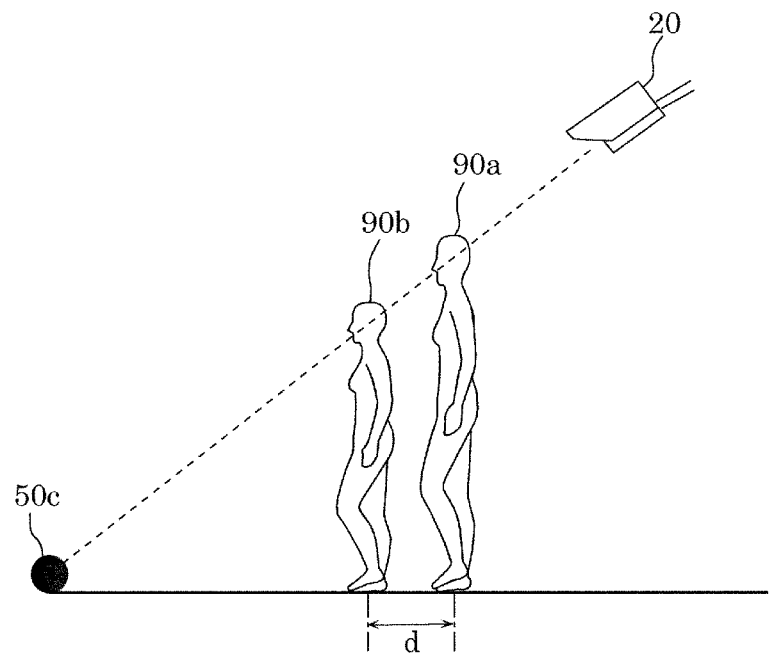
FIG. 11 is a schematic diagram illustrating a deviation in position of the person to be evaluated depending on a height thereof.

As described above, calculation unit 12a processes the video data on person-to-be-evaluated 90 during walking on the predetermined interval between marker 50a and marker 50b. In this case, for example, when the camera installed in a ceiling or the like images person-to-be-evaluated 90 with an angle at which person-to-be-evaluated 90 is looked down from above, the determination as to whether person-to-be-evaluated 90 has passed through the predetermined interval may vary depending on the height of person-to-be-evaluated 90. FIG. 11 is a schematic diagram illustrating a deviation in the position of person-to-be-evaluated 90 depending on the height.

As illustrated in FIG. 11, the position of person-to-be-evaluated 90a when the head portion of person-to-be-evaluated 90a overlaps marker 50c as viewed from camera 20 and the position of person-to-be-evaluated 90b when the head portion of person-to-be-evaluated 90b overlaps marker 50c deviate from each other by distance d.

Accordingly, calculation unit 12a may correct the position of person-to-be-evaluated 90a in the video data depending on the height of person-to-be-evaluated 90a. In this case, for example, height information about person-to-be-evaluated 90a is stored in storage unit 13. Note that instead of using storage unit 13 as a height information storage unit, cognitive function evaluation device 10 may include the height information storage unit separately from storage unit 13.

Calculation unit 12a can correct the position of person-to-be-evaluated 90a in the video data by using the height information stored in storage unit 13 using, for example, a predetermined height (e.g., 160 cm) as a standard. When the height of person-to-be-evaluated 90a is 170 cm, calculation unit 12a determines whether person-to-be-evaluated 90a has passed through the predetermined interval in consideration of distance d corresponding to the height difference of 10 cm. Specifically, calculation unit 12a can specify a period in which person-to-be-evaluated 90a walks on the predetermined interval in the video data based on the corrected position of person-to-be-evaluated 90a. A period in which person-to-be-evaluated 90b walks on the predetermined interval can also be specified by a similar method.

Note that in the height information, the height information about a plurality of persons-to-be-evaluated 90 may be associated with face image data on person-to-be-evaluated 90. With this configuration, calculation unit 12a can specify the height information of person-to-be-evaluated 90 during walking within the image-capturing range of camera 20 by using a face recognition technique. Note that when an image of the face of person-to-be-evaluated 90 cannot be captured by camera 20, a camera for face recognition may be installed separately from camera 20 at a position where an image of the face of person-to-be-evaluated 90 can be captured.

[Advantageous Effects and the Like of Embodiment 1]

As described above, cognitive function evaluation device 10 includes acquisition unit 11 that acquires body motion data representing a body motion of person-to-be-evaluated 90 during walking, calculation unit 12a that calculates a displacement of the body of person-to-be-evaluated 90 during walking based on the acquired body motion data, and evaluation unit 12b that evaluates the cognitive function of person-to-be-evaluated 90 based on a frequency peak representing a cycle of walking of person-to-be-evaluated 90 that is obtained by performing a frequency analysis on the calculated displacement, and outputs the evaluation result.

With this configuration, cognitive function evaluation device 10 can evaluate the cognitive function of person-to-be-evaluated 90 based on the periodicity of walking of person-to-be-evaluated 90. According to cognitive function evaluation device 10, it is only necessary for person-to-be-evaluated 90 to walk to evaluate the cognitive function thereof. In other words, cognitive function evaluation device 10 can easily evaluate the cognitive function.

Furthermore, evaluation unit 12b may evaluate the cognitive function of person-to-be-evaluated 90 such that the cognitive function of person-to-be-evaluated 90 deteriorates as the peak level decreases, based on the peak level of the frequency peak.

With this configuration, cognitive function evaluation device 10 can evaluate the cognitive function of person-to-be-evaluated 90 based on the frequency peak.

Furthermore, evaluation unit 12b may evaluate the cognitive function of person-to-be-evaluated 90 such that the cognitive function of person-to-be-evaluated 90 deteriorates as the half width of the frequency peak increases, based on the half width of the frequency peak.

With this configuration, evaluation unit 12b can evaluate the cognitive function of person-to-be-evaluated 90 based on a variation in the frequency peak (increase in the skirt of the frequency peak).

Furthermore, calculation unit 12a may calculate a displacement in the up-down direction of the body of person-to-be-evaluated 90 during walking based on the acquired body motion data, and evaluation unit 12b may evaluate the cognitive function of person-to-be-evaluated 90 based on the frequency peak obtained by performing a frequency analysis on the calculated displacement in the up-down direction.

With this configuration, cognitive function evaluation device 10 can evaluate the cognitive function of person-to-be-evaluated 90 based on the periodicity of walking of person-to-be-evaluated 90 that is determined depending on the displacement in the up-down direction of the body of person-to-be-evaluated 90 during walking.

Furthermore, cognitive function evaluation device 10 may further include storage unit 13 that stores reference data representing a relationship between information about the frequency peak representing the cycle of walking of a person and the cognitive function of the person. Evaluation unit 12b may evaluate the cognitive function of person-to-be-evaluated 90 by comparing the frequency peak representing the cycle of walking of person-to-be-evaluated 90 with the reference data stored in storage unit 13.

With this configuration, cognitive function evaluation device 10 can evaluate the cognitive function of person-to-be-evaluated 90 based on the reference data.

Furthermore, acquisition unit 11 may acquire, as body motion data, video data on person-to-be-evaluated 90 during walking that is captured by camera 20, and calculation unit 12a may calculate a displacement of the body of person-to-be-evaluated 90 during walking by performing image processing on the video data.

With this configuration, cognitive function evaluation device 10 can evaluate the cognitive function of person-to-be-evaluated 90 based on the periodicity of walking of person-to-be-evaluated 90 that is determined based on the video data on person-to-be-evaluated 90. Furthermore, it is only necessary for person-to-be-evaluated 90 to walk to evaluate the cognitive function thereof. In other words, cognitive function evaluation device 10 can easily evaluate the cognitive function.

Furthermore, acquisition unit 11 may acquire the video data captured by camera 20 during walking of person-to-be-evaluated 90 in a space in which two markers representing a start point and end point of a predetermined interval are arranged. In the image processing, calculation unit 12a may specify a period in which person-to-be-evaluated 90 walks on the predetermined interval in the video data, and may calculate a displacement of the body of person-to-be-evaluated 90 during walking in the period.

With this configuration, cognitive function evaluation device 10 can evaluate the cognitive function of person-to-be-evaluated 90 based on the periodicity of walking of person-to-be-evaluated 90 that is determined based on the video data on person-to-be-evaluated 90 during walking between the two markers.

Furthermore, cognitive function evaluation device 10 may further include storage unit 13 that stores height information about person-to-be-evaluated 90. Calculation unit 12a may correct the position of person-to-be-evaluated 90 in the video data by using the height information stored in storage unit 13, and may specify a period in which person-to-be-evaluated 90 walks on the predetermined interval in the video data based on the corrected position of person-to-be-evaluated 90. Storage unit 13 is an example of the height information storage unit.

With this configuration, cognitive function evaluation device 10 may determine whether person-to-be-evaluated 90 has passed through the predetermined interval, thereby suppressing a variation depending on the height of person-to-be-evaluated 90.

Furthermore, cognitive function evaluation system 100 includes cognitive function evaluation device 10 and camera 20 that generates the video data. Camera 20 is an example of the body motion data generation device, and the video data is an example of the body motion data.

With this configuration, cognitive function evaluation system 100 can evaluate the cognitive function of person-to-be-evaluated 90 based on the periodicity of walking of person-to-be-evaluated 90 that is determined based on the video data on person-to-be-evaluated 90.

Furthermore, the cognitive function evaluation method to be executed by cognitive function evaluation device 10 or cognitive function evaluation system 100 acquires body motion data representing a body motion of person-to-be-evaluated 90 during walking, calculates a displacement of the body of person-to-be-evaluated 90 during walking based on the acquired body motion data, evaluates the cognitive function of person-to-be-evaluated 90 based on the frequency peak representing the cycle of walking of person-to-be-evaluated 90 that is obtained by performing a frequency analysis on the calculated displacement, and outputs the evaluation result.

The cognitive function evaluation method as described above is capable of evaluating the cognitive function of person-to-be-evaluated 90 based on the periodicity of walking of person-to-be-evaluated 90.

Embodiment 2

[Functional Configuration of Cognitive Function Evaluation System According to Embodiment 2]

In Embodiment 1 described above, the video data captured by camera 20 is used as the body motion data. However, cognitive function evaluation system 100 and cognitive function evaluation device 10 may evaluate the cognitive function by using body motion data other than the video data.

Figure 12:
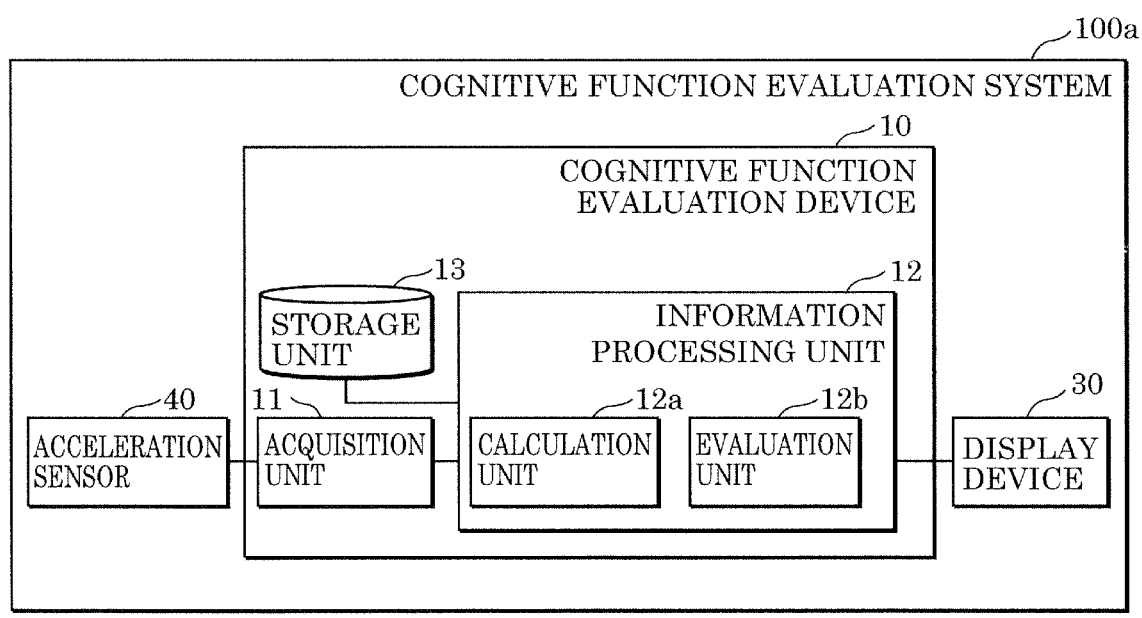
FIG. 12 is a block diagram illustrating a functional configuration of a cognitive function evaluation system according to Embodiment 2.

For example, data representing an acceleration of the body motion measured by an acceleration sensor (hereinafter referred to as acceleration data) may be used as the body motion data. Such a cognitive function evaluation system and a cognitive function evaluation device according to Embodiment 2 will be described below. FIG. 12 is a block diagram illustrating a functional configuration of the cognitive function evaluation system according to Embodiment 2. Note that in the following Embodiment 2, differences between Embodiment 2 and Embodiment 1 will be mainly described, and features that have already been described in Embodiment 1 will be omitted as needed.

As illustrated in FIG. 12, cognitive function evaluation system 100a according to Embodiment 2 includes acceleration sensor 40 instead of camera 20. Acceleration sensor 40 is worn by person-to-be-evaluated 90, and the acceleration data on person-to-be-evaluated 90 during walking is output as the body motion data. Acceleration sensor 40 is an example of the body motion data generation device, and the acceleration data is an example of the body motion data.

Acquisition unit 11 acquires, as the body motion data, the acceleration data on the body motion measured by acceleration sensor 40. The acquired acceleration data is stored, for example, in storage unit 13 by information processing unit 12.

Figure 13:
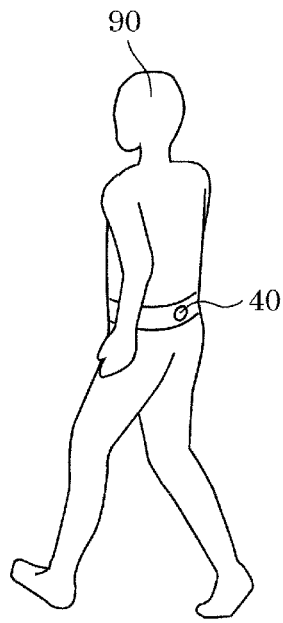
FIG. 13 is a diagram illustrating an acceleration sensor worn around a waist of the person to be evaluated.

Acceleration sensor 40 is worn, for example, around a waist portion of person-to-be-evaluated 90. FIG. 13 is a diagram illustrating acceleration sensor 40 worn around the waist portion of person-to-be-evaluated 90. Acceleration sensor 40 is worn by person-to-be-evaluated 90 in such a manner that, for example, a measurement axis is set along a vertical direction (up-down direction), but instead may be worn by person-to-be-evaluated 90 in such a manner that the measurement axis is set along a horizontal direction (right-left direction or front-back direction).

[Cognitive Function Evaluation Method According to Embodiment 2]

Figure 14:
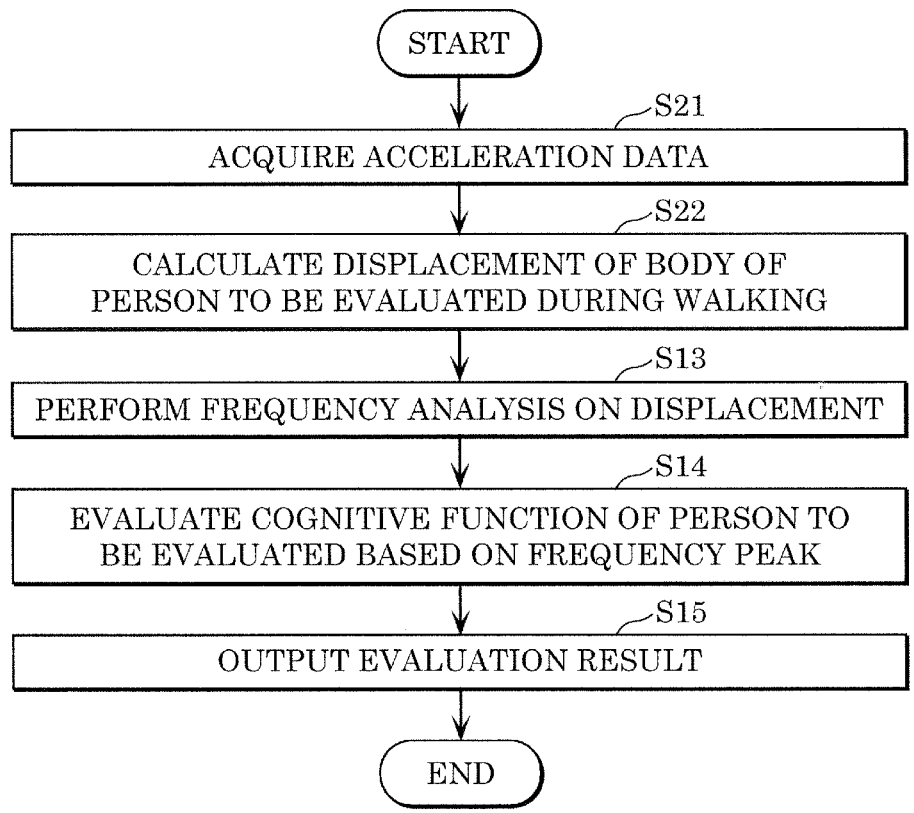
FIG. 14 is a flowchart illustrating a cognitive function evaluation method according to Embodiment 2.

Next, a cognitive function evaluation method according to Embodiment 2 will be described. FIG. 14 is a flowchart illustrating the cognitive function evaluation method according to Embodiment 2.

Figure 15:
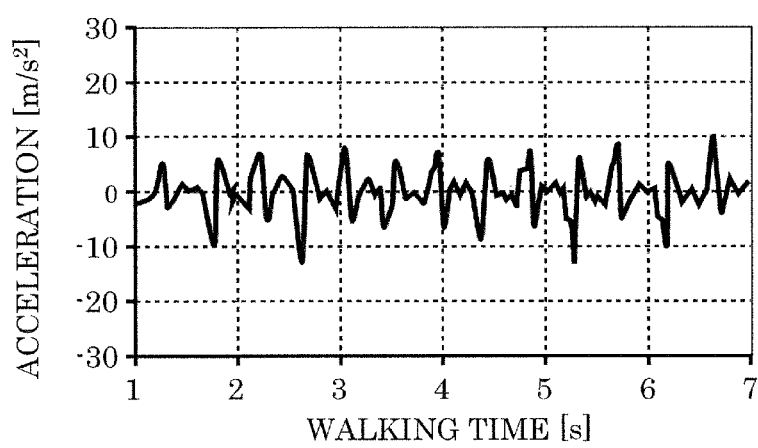
FIG. 15 is a diagram illustrating an example of acceleration data.

In the cognitive function evaluation method according to Embodiment 2, first, acquisition unit 11 acquires the acceleration data measured by acceleration sensor 40 as the body motion data (S21). Acquisition unit 11 acquires the acceleration data by, for example, wireless communication, but instead may acquire the acceleration data by wired communication. The acceleration data represents, for example, a signal as illustrated in FIG. 15. FIG. 15 is a diagram illustrating an example of the acceleration data.

Next, calculation unit 12a calculates a displacement of the body of person-to-be-evaluated 90 during walking based on the acquired acceleration data (S22). The subsequent processing (steps S13 to S15) is similar to that in Embodiment 1.

Figure 16:
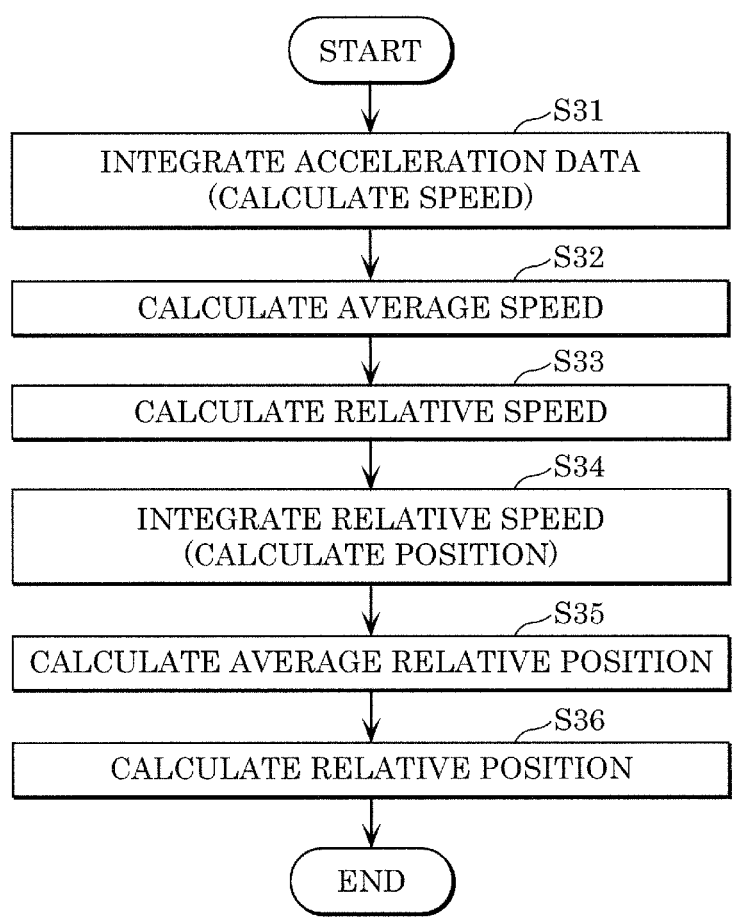
FIG. 16 is a flowchart illustrating a method for calculating a displacement of the body of the person to be evaluated during walking according to Embodiment 2.

A method for calculating the displacement of the body of person-to-be-evaluated 90 during walking in step S22 will now be described in detail. FIG. 16 is a flowchart illustrating the method for calculating the displacement of a body of person-to-be-evaluated 90 during walking according to Embodiment 2.

First, calculation unit 12a calculates a speed by integrating acceleration (S31). Next, calculation unit 12a calculates an average speed of the calculated speed (S32). Then, calculation unit 12a calculates a speed relative to the average speed based on the speed calculated in step S31 and the average speed calculated in step S32 (S33).

Subsequently, calculation unit 12a calculates positions by integrating the calculated relative speed (S34). Furthermore, calculation unit 12a calculates an average relative position as an average of the calculated positions (S35). Then, calculation unit 12a calculates a position relative to the average relative position based on the position calculated in step S34 and the average relative position calculated in step S35 (S36). The calculated relative position represents a signal as illustrated in FIG. 5 described above. Specifically, the calculated relative position represents a displacement of the body of person-to-be-evaluated 90 during walking.

Advantageous Effects and the Like of Embodiment 2

As described above, in cognitive function evaluation system 100a according to Embodiment 2, acquisition unit 11 acquires, as the body motion data, data representing the acceleration of the body motion measured by acceleration sensor 40 worn by person-to-be-evaluated 90. Calculation unit 12a calculates the displacement of the body of person-to-be-evaluated 90 during walking by integrating the acceleration. Acceleration sensor 40 is an example of the body motion data generation device, and the acceleration data is an example of the body motion data.

With this configuration, cognitive function evaluation system 100a (cognitive function evaluation device 10 included in cognitive function evaluation system 100a) can evaluate the cognitive function of person-to-be-evaluated 90 based on the periodicity of walking of person-to-be-evaluated 90 that is determined based on the acceleration data. Furthermore, it is only necessary for person-to-be-evaluated 90 to walk to evaluate the cognitive function thereof. In other words, cognitive function evaluation system 100a (cognitive function evaluation device 10 included in cognitive function evaluation system 100a) can easily evaluate the cognitive function.

Modified Example of Embodiment 2

Figure 17:
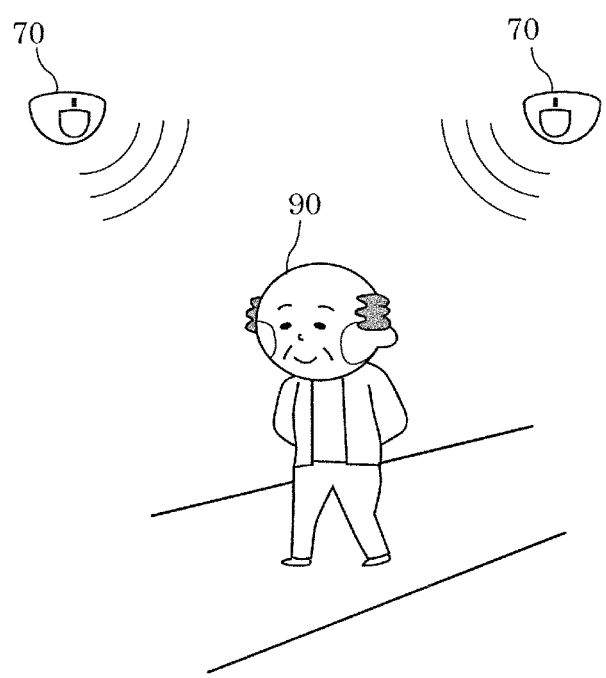
FIG. 17 is a diagram for explaining an outline of a cognitive function evaluation system including a radio wave sensor.

Note that cognitive function evaluation system 100a may include a radio wave sensor instead of acceleration sensor 40. FIG. 17 is a diagram for explaining an outline of the cognitive function evaluation system including the radio wave sensor.

Radio wave sensor 70 can emit, for example, a microwave, and can detect a change in the frequency of a reflected wave, which is reflected by person-to-be-evaluated 90, with respect to the frequency of the emitted microwave. Radio wave sensor 70 is an example of the body motion data generation device.

According to radio wave sensor 70, a motion of person-to-be-evaluated 90, i.e., a displacement of the body of person-to-be-evaluated 90 during walking can be detected. According to radio wave sensor 70, the cognitive function evaluation system can evaluate the cognitive function of person-to-be-evaluated 90 based on the periodicity of walking of person-to-be-evaluated 90 that is determined based on an output from radio wave sensor 70.

Other Embodiments

While the cognitive function evaluation device and the cognitive function evaluation system according to the embodiments have been described above, the present invention is not limited to the embodiments described above.

Furthermore, the distribution of the components included in the cognitive function evaluation device described in the above embodiments to each device is merely an example. The components included in the cognitive function evaluation system may be arbitrarily distributed within a range in which the degree of dementia of the user can be determined. For example, the storage unit included in the cognitive function evaluation device may be implemented as a single storage device.

Furthermore, the cognitive function evaluation system may be implemented by a client server system. In this case, for example, the cognitive function evaluation device is implemented as a server device, and the display device such as a personal computer, a smartphone, or a tablet terminal is implemented as a client device The communication method between the devices described in the above embodiment is an example. The communication method between the devices is not particularly limited. Wireless communication between the devices is established using communication standards such as a specified low-power wireless communication, ZigBee®, Bluetooth®, or Wi-Fi®. Note that specific examples of the wireless communication include radio wave communication and infrared communication.

Instead of wireless communication, wired communication, such as power line communication (PLC) or communication using a wired LAN, may be established between the devices.

While each component is configured using dedicated hardware in the above embodiments, each component may be implemented by executing a software program suitable for each component. Each component may also be implemented in such a manner that a program execution unit, such as a CPU or a processor, reads out a software program recorded in a recording medium, such as a hard disk or a semiconductor memory, and executes the read software program.

Furthermore, each component may be a circuit (or an integrated circuit). These circuits may constitute one circuit as a whole, or may be separate circuits. Furthermore, these circuits may be general-purpose circuits or dedicated circuits.

Furthermore, the overall or specific forms of the present invention may be implemented by a system, a device, a method, an integrated circuit, a computer program, or a recording medium such as a computer-readable CD-ROM. Furthermore, the present invention may also be implemented by any combination of a system, a device, a method, an integrated circuit, a computer program, and a recording medium. For example, the present invention may be implemented as a program for causing a computer to execute the cognitive function evaluation method according to the above embodiment, or may be implemented as a non-transitory recording medium storing the program.

Furthermore, the order of a plurality of processes in the flowchart of the cognitive function evaluation method described in the above embodiment is merely an example. The order of the plurality of processes may be changed, or the plurality of processes may be executed in parallel. Furthermore, another processing unit may execute processing executed by a specific processing unit.

In addition, forms obtained by modifying the embodiments in various ways that can be conceived by a person skilled in the art and forms implemented by arbitrarily combining the components and functions in each embodiment without departing from the scope of the present invention are also included in the present invention.

The invention claimed is:

1. A cognitive function evaluation device, comprising:
a communication circuit configured to acquire body motion data representing a body motion of a person to be evaluated during walking;
a processor;
a non-transitory memory storing a program, wherein:
the program, when executed by the processor, causes the processor to function as:
a calculation unit configured to calculate a displacement of a body of the person to be evaluated during walking based on the body motion data acquired, and calculate a cycle of walking of the person to be evaluated by performing a frequency analysis on the displacement calculated; and
an evaluation unit configured to evaluate a cognitive function of the person to be evaluated based on a frequency peak representing the cycle of walking of the person to be evaluated, and to display an evaluation result on a display device, the evaluation unit is configured to evaluate the cognitive function of the person to be evaluated based on a half width of the frequency peak, and evaluate that the cognitive function of the person to be evaluated deteriorates as the half width increases, the evaluation unit displays on the display device:
- a first evaluation result of the cognitive function of the person to be evaluated in a first display mode, when the cognitive function of the person to be evaluated is normal; and
- a second evaluation result of the cognitive function of the person to be evaluated in a second display mode, when the cognitive function of the person to be evaluated is deteriorated, and the second display mode includes warning information recommending the person to be evaluated to seek medical attention.

2. The cognitive function evaluation device according to claim 1,
wherein the calculation unit is configured to calculate a displacement in an up-down direction of the body of the person to be evaluated during walking based on the body motion data acquired, and
the evaluation unit is configured to evaluate the cognitive function of the person to be evaluated based on the frequency peak obtained by performing the frequency analysis on the displacement in the up-down direction calculated.

3. The cognitive function evaluation device according to claim 1, further comprising:
a storage unit configured to store reference data representing a relationship between the cognitive function of the person and information about the frequency peak representing the cycle of walking of the person,
wherein the evaluation unit is configured to evaluate the cognitive function of the person to be evaluated by comparing the frequency peak representing the cycle of walking of the person to be evaluated with the reference data stored in the storage unit.

4. The cognitive function evaluation device according to claim 1, wherein:
the communication circuit is configured to acquire, as the body motion data, video data of the person to be evaluated during walking, the video data being captured by a camera, and
the calculation unit is configured to calculate the displacement of the body of the person to be evaluated during walking by performing image processing on the video data.

5. The cognitive function evaluation device according to claim 4, wherein:
the communication circuit is configured to acquire the video data captured by the camera during walking of the person to be evaluated in a space in which two markers representing a start point and an end point of a predetermined interval are arranged, and
in the image processing, the calculation unit is configured to specify a period in which the person to be evaluated walks on the predetermined interval in the video data, and calculate the displacement of the body of the person to be evaluated during walking in the period.

6. The cognitive function evaluation device according to claim 5, further comprising:
a height information storage unit configured to store height information about the person to be evaluated,
wherein the calculation unit is configured to correct a position of the person to be evaluated in the video data by using the height information stored in the height information storage unit, and specify the period in which the person to be evaluated walks on the predetermined interval in the video data based on the corrected position of the person to be evaluated.

7. The cognitive function evaluation device according claim 1, wherein:
the communication circuit is configured to acquire, as the body motion data, data representing an acceleration of the body motion measured by an acceleration sensor worn by the person to be evaluated, and
the calculation unit is configured to calculate the displacement of the body of the person to be evaluated during walking by integrating the acceleration.

8. A cognitive function evaluation system, comprising:
the cognitive function evaluation device according to claim 1, and
a body motion data generation device configured to generate the body motion data.

9. The cognitive function evaluation device according to claim 1, wherein the frequency analysis comprises discrete Fourier transformation.

10. A cognitive function evaluation method, comprising:
acquiring, by using a communication circuit, body motion data representing a body motion of a person to be evaluated during walking;
calculating, by using a computer, a displacement of a body of the person to be evaluated during walking based on the body motion data acquired;
calculating, by using the computer, a cycle of walking of the person to be evaluated by performing a frequency analysis on the displacement calculated;
evaluating, by using the computer, a cognitive function of the person to be evaluated based on a half width of a frequency peak representing the cycle of walking of the person to be evaluated such that the cognitive function of the person to be evaluated deteriorates as the half width increases; and
displaying:
- a first evaluation result of the cognitive function of the person to be evaluated in a first display mode, when the cognitive function of the person to be evaluated is normal; and
- a second evaluation result of the cognitive function of the person to be evaluated in a second display mode, when the cognitive function of the person to be evaluated is deteriorated, wherein the second display mode includes warning information recommending the person to be evaluated to seek medical attention.

11. A non-transitory computer-readable recording medium having recorded thereon a program for causing a computer to execute the cognitive function evaluation method according to claim 10.

12. The cognitive function evaluation method according to claim 10, wherein the frequency analysis comprises discrete Fourier transformation.

* * * * *